May 8, 1973 F. W. ANDERSON Plant Pat. 3,329
NECTARINE TREE
Filed Sept. 29, 1971
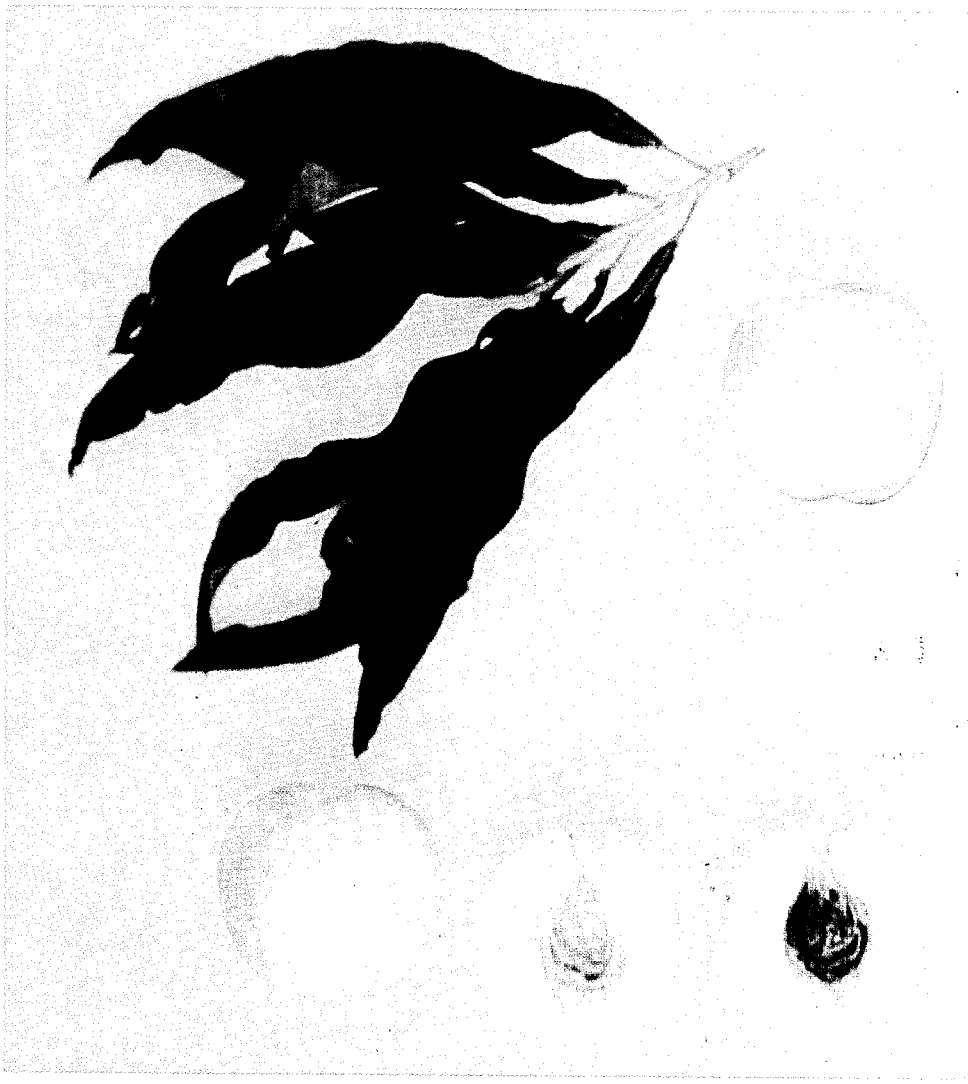

United States Patent Office

Plant Pat. 3,329
Patented May 8, 1973

3,329

NECTARINE TREE

Frederic W. Anderson, Merced, Calif., assignor to Arthur Bright, Le Grand, Calif.

Filed Sept. 29, 1971, Ser. No. 184,968
Int. Cl. A01h 5/03
U.S. Cl. Plt.—41 1 Claim

ABSTRACT OF THE DISCLOSURE

A nectarine tree, of genetic dwarf type, which is of medium size with a mature height of five to eight feet, medium vigorous, spreading, dense, and productive of large to medium size uniformly globose freestone fruit having yellow skin substantially overspread with red and yellow flesh, the surface of the pit cavity being red, and the stone being brown; the fruit averaging somewhat larger than, and being in harvest over a month before, the Golden Prolific nectarine (United States Plant Patent No. 2,193), and in harvest approximately with the Red Haven peach (unpatented).

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present vairety of nectarine tree was originated by me in the aforesaid experimental nursery and orchard as a cross between two unnamed, dwarf seedlings (unpatented). The seedling resulting from such cross was maintained by me under careful and continuing observation, and—upon bearing fruit—such seedling (which is the present variety) was recognized by me as having certain new and distinct characteristics desirable for a commercial nectarine tree. I, therefore, undertook asexual reproduction of the variety in anticipation of its ultimate introduction to the trade.

ASEXUAL REPRODUCTION OF THE VARIETY

Subsequent to origination by me of the present variety of nectarine tree, in the manner above described, I asexually reproduced it by top-working on mature nectarine trees in my said experimental orchard, and—in maturity—such reproductions ran true to the original tree in all respects.

SUMMARY OF THE VARIETY

The herein claimed new and distinct variety of genetic dwarf nectarine tree is of medium size with a mature height of five to eight feet, medium vigorous, spreading, dense, and productive of large to medium size uniformly globose freestone fruit having yellow skin substantially overspread with red and yellow flesh, the surface of the pit cavity being red, and the stone being brown; the fruit averaging somewhat larger than, and being in harvest over a month before, the Golden Prolific nectarine, and in harvest approximately with the Red Haven peach.

While the fruit of the present variety of dwarf nectarine tree can be manually harvested—advantageously—without the use of ladders, such fruit is of a quality which permits of both local and long distance shipping, and thereafter has an adequate shelf life to compete commercially with the fruit of nectarine varieties which have full size trees.

BRIEF DESCRIPTION OF THE DRAWING

The drawing is an illustration, by photographic reproduction in color, of leaves and fruit of the variety; one fruit being cut into halves, with the stone remaining in one half.

DESCRIPTION OF THE VARIETY

The botanical details of this new and distinct variety of nectarine tree—with color definitions referenced to Maerz and Paul Dictionary of Color—are as follows:

Tree:
- *Type.*—Dwarf.
- *Size.*—Medium, average height—5′ to 8′.
- *Vigor.*—Medium.
- *Growth.*—Spreading.
- *Density.*—Dense.
- *Production.*—Productive.

Trunk:
- *Size.*—Medium
- *Texture.*—Medium.

Branches:
- *Size.*—Medium.
- *Texture.*—Smooth.

Leaves:
- *Size.*—Large, average length—7″, average width—⅞″.
- *Form.*—Lanceolate, acutely pointed.
- *Thickness.*—Thick.
- *Margin.*—Crenate.
- *Petiole.*—Medium length, medium thickness.
- *Glands.*—Number and position—usually 2 or 3 on blade and 2 on petiole. Alternate, reniform.
- *Color.*—Top side—medium green (22–K–7), under side—lighter green (21–K–7).

Flower buds:
- *Size.*—Large.
- *Length.*—Medium.
- *Form.*—Plump.

Flowers:
- *Blooming period.*—Early to medium, as compared with other varieties.
- *Date of first bloom.*—Mar. 4, 1971.
- *Date of full bloom.*—Mar. 15, 1971.
- *Size.*—Large, showy.

Fruit:
- *Maturity when described.*—Eating ripe—July 18, 1971.
- *Date of first picking.*—July 15, 1971.
- *Date of last picking.*—July 25, 1971.
- *Size.*—Large to medium, average diameter axially—2½″, average transversely in suture plane—2 9/16″.
- *Form.*—Uniform, globose.
- *Suture.*—Conspicuously distinct, extends from base to apex, marked depression beyond pistil point.
- *Cavity.*—Circular.
- *Base.*—Rounded.
- *Apex.*—Very short.
- *Pistil point.*—Extremely small.

Skin:
- *Thickness.*—Medium.
- *Texture.*—Medium.
- *Tendency to crack.*—Slight.
- *Down.*—Wanting.
- *Color.*—Yellow (10–L–7) substantially overspread with red (6–L–9), mottled and speckled.

Flesh:
- *Ripens.*—Evenly.
- *Flavor.*—Subacid to mild, flat.
- *Aroma.*—Distinct.
- *Eating quality.*—Good to best.
- *Color.*—Yellow (10–K–5).

*Surface of pit cavity.*—Red (5–L–6).

Stone:

*Type.*—Free.

*Size.*—Medium, average length—1⅜", average breadth—¾", average thickness—½".

*Color.*—Brown (15–A–10).

Use: Market—local and long distance shipping.

Keeping quality: Medium.

Resistance to insects and diseases: No unusual susceptibilities noted.

Shipping quality: Good.

The nectarine tree and its fruit herein described may vary in slight detail due to climatic and soil conditions under which the variety may be grown; the present description being of the vairety as grown in the Central Valley of California.

I claim:

1. A new and distinct variety of genetic dwarf nectarine tree, substantially as illustrated and described, which is of medium size with a mature height of five to eight feet, medium vigorous, spreading, dense, and productive of large to medium size uniformly globose freestone fruit having yellow skin substantially overspread with red and yellow flesh, the surface of the pit cavity being red, and the stone being brown; the fruit averaging somewhat larger than, and being in harvest over a month before, the Golden Prolific nectarine, and in harvest approximately with the Red Haven peach.

No references-cited.

ROBERT E. BAGWILL, Primary Examiner